United States Patent
Munari et al.

(10) Patent No.: US 6,579,345 B2
(45) Date of Patent: Jun. 17, 2003

(54) CHROMATOGRAPHY APPARATUS WITH DIRECT HEATING OF THE CAPILLARY COLUMN

(75) Inventors: Fausto Munari, Milan (IT); Giancinto Zillioli, Cernusco Sul Naviglio (IT); Roberto Raffaeta, Carisolo (IT); Riccardo Facchetti, Lecco (IT); Paolo Magni, Besana Brianza (IT)

(73) Assignee: Thermo Finnigan Italia S.p.A., Milan (IT)

( * ) Notice: Subject to any disclaimer, the term of this patent is extended or adjusted under 35 U.S.C. 154(b) by 0 days.

(21) Appl. No.: 09/868,555

(22) PCT Filed: Dec. 21, 2000

(86) PCT No.: PCT/IT00/00541

§ 371 (c)(1),
(2), (4) Date: Dec. 10, 2001

(87) PCT Pub. No.: WO01/48469

PCT Pub. Date: Jul. 5, 2001

(65) Prior Publication Data

US 2002/0178912 A1 Dec. 5, 2002

(30) Foreign Application Priority Data

Dec. 27, 1999 (IT) ............................ MI99A2708

(51) Int. Cl.⁷ .............................................. B01D 15/08
(52) U.S. Cl. .................................. 95/87; 95/82; 96/102
(58) Field of Search ............... 95/17, 18, 82–89; 96/101–107

(56) References Cited

U.S. PATENT DOCUMENTS

| | | | | |
|---|---|---|---|---|
| 3,305,000 A | * | 2/1967 | Bullen et al. | 96/102 X |
| 4,726,822 A | * | 2/1988 | Cates et al. | 96/101 |
| 4,923,486 A | * | 5/1990 | Rubey | 95/87 |
| 5,005,399 A | * | 4/1991 | Holtzclaw et al. | 73/23.39 |
| 5,028,243 A | * | 7/1991 | Rubey | 95/87 |

(List continued on next page.)

OTHER PUBLICATIONS

Copy of International Search Report for PCT/IT00/00541 dated Aug. 10, 2001.
Eijkel J C T et al: "Micromachined Heated Chemical Reactor for Pre–column Derivatisation" Journal of Chromatography A, Elsevier Science, NL, vol. 815, No. 2—Jul. 31, 1998, pp. 265–271 XP004145824 ISSN: 0021–9673, p. 269.
Brandt A et al: "Temperature Gradients in Preparative High–Performance Liquid Chromatography Columns" Journal of Chromatography A, Elsevier Science, NL. vol. 769, No. 1 May 2, 1997, pp. 109–117, XP004064211.
De Geus H et al: "Development of a Thermal Desorption Modulator for Gas Chromatography" Journal of Chromatography A, Elsevier Science, NL vol. 767, No. 1–2, Apr. 11, 1997, pp. 137–151.
Es Van A et al.: "Sample Enrichment in High Speed Narrow Bore Capillary Gas Chromatography" Journal of High Resolution Chromatography and Chromatography Communications Dr. Alfred Huethig Verlag, Heidelberg, DE vol. 11, Dec. 11, 1988, pp. 852–857.

Primary Examiner—Robert H. Spitzer
(74) Attorney, Agent, or Firm—Gibbons, Del Deo, Dolan, Griffinger & Vecchione (57) ABSTRACT

A method and an apparatus for chromatography are described, wherein at least one element in electrically conductive material is provided to heat the capillary column in a direct way and wherein the control of the temperature is carried out according to a mathematical model having a component of predictive type, or Feed Forward type, that describes the thermodynamic behavior of the assembly comprising the electrically conductive element and the column at least as a function of the thermal resistance and the thermal capacity of the assembly thus constituted in order to regulate the supply of electrical power supplied to the conductive element.

30 Claims, 6 Drawing Sheets

U.S. PATENT DOCUMENTS

| | | | | |
|---|---|---|---|---|
| 5,032,151 A | * | 7/1991 | Klein et al. | 95/18 X |
| 5,114,439 A | * | 5/1992 | Yost et al. | 55/20 |
| 5,135,549 A | * | 8/1992 | Phillips et al. | 95/87 X |
| 5,544,276 A | * | 8/1996 | Loux et al. | 96/102 X |
| 5,588,988 A | * | 12/1996 | Gerstel et al. | 96/101 |
| 5,596,876 A | * | 1/1997 | Manura et al. | 95/87 X |
| 5,611,846 A | * | 3/1997 | Overton et al. | 96/102 |
| 5,634,961 A | * | 6/1997 | Gordon | 95/18 X |
| 5,782,964 A | * | 7/1998 | Mustacich | 96/102 |
| 5,808,178 A | * | 9/1998 | Rounbehler et al. | 73/23.39 |
| 6,103,112 A | * | 8/2000 | Sutton et al. | 95/87 X |
| 6,209,386 B1 | * | 4/2001 | Mustacich et al. | 95/87 X |

* cited by examiner

CHROMATOGRAPHY APPARATUS WITH DIRECT HEATING OF THE CAPILLARY COLUMN

TECHNICAL FIELD

The present invention relates to apparatus for chromatography in which the capillary column is heated directly and to a method of controlling the temperature of the capillary column.

BACKGROUND ART

It is known in the art that direct heating of the column confers various advantages, among which is a considerable reduction in the quantity of electrical power required to heat the column by means of an element made of electrically conductive material which encircles the same capillary column.

An example of a portable gas chromatography apparatus with direct heating of the column is described in U.S. Pat. No. 5,611,846 by Overton et al. In order to directly heat the column, this document suggests inserting the column into a sheath together with a conductive filament, or inserting the column directly into a tube made of conductive material. The hypothesis of using columns covered with conductive material—such as, for example, columns in fused silica covered with a thin layer of aluminum—had already been rejected because of frequent breakage of the column or the covering conductor due to the different coefficients of thermal expansion of the materials.

As a temperature sensor, the Overton patent suggests to use a filament made of conductive material inserted into the sheath or the conductive tube in close contact with the column but insulated electrically from the other conductive element (tube or filament) used to heat the column. A control device able to determine the temperature of the conductor as a function of its resistance is employed to regulate the heating of the column. The control device cyclically compares the set temperature with that calculated on the basis of the temperature sensor signal and corrects the power supplied to the heating conductor by varying the voltage applied to the same. Moreover, the possibility of using the same heating conductor as temperature sensor Is also suggested, without however specifying what kind of control device could be suitable for this particular embodiment.

While not specifying which type of control was used In the system of the cited US patent, it was asserted that the system is able to control temperature ramps of slope up to 10° C./sec. This parameter confirms that the direct heating of the column can be efficient from the point of view of the rapidity of response of the system, but is opportune to point out that obtaining similar heating speeds with an Inadequate control device could compromise the stability and the precision of the system in Its entirety.

In fact, it has been subsequently found that this type of system has shortcomings-related to both the precision of temperature measurement with respect to conventional chromatography apparatus with oven heating, and to the repeatability of the set temperature profiles for Identical analyses (see "Novel Column Heater for Fast Capillary Gas Chromatography"; Overton et al—-Journal of Chromatographic Science—Vol.34 —December 1996, for example). U.S. Pat. No. 5,114,439 by Yost et al describes a chromatography apparatus in which the column is covered with a film of conductive material. This document confirms substantially the effectiveness of the column direct heating technology, but it is opportune to emphasize that the use of columns covered with conductive films involves the disadvantages already identified by Overton referred to previously. As temperature control device, the Yost patent suggests the use of a PID-type industrial controller to control by feedback the electrical supply to the conductor associated with the column.

A system for heating the column by means of a tube conductor which contains the same column is illustrated in U.S. Pat. No. 5,808,178 and in the corresponding international patent application n. WO 97/14957 in the name of Thermedics. The temperature control system alternates cycles of supplying constant high voltage to heat the tube conductor, with measurement cycles of more limited constant voltage to measure the resistance of the tube conductor and, consequently, the temperature of the tube/column system. Moreover, the use of standard PI or PID type standard industrial controllers is suggested as an improvement of a similar system.

However, it should be noted that even PID type standard controllers are inadequate to guarantee the necessary temperature control precision when particularly high heating speeds are applied.

A slightly improved column temperature control system is described in U.S. Pat. No. 5,005,399 by Holtzclaw et al. Also in this case, the heating system provides for the use of a column covered with a conductive film, therefore subject to all the disadvantages already previously cited. However, to control the heating temperature, a control device is suggested in which a pseudo-derivative correction factor is introduced into the feedback control of the temperature or, rather, of the voltage applied to the conductive material which covers the column. One of the main disadvantages of this system lies in the fact that, to maintain the correct operation of the column within the specified limits of error (±1° C.), particularly precise calibration of the gain of every component of the control system is required. The calibration operations necessarily demand a certain skill and experience, and they are necessary every time the column is replaced.

The object of the present invention is to propose a chromatography apparatus with direct heating of the column that gives particularly precise control of the temperature of the column.

Another object of the present invention is to propose a chromatography apparatus with direct heating of the column that can guarantee high response speed, maintaining in any case the necessary precision with respect to the set temperature profiles, be they linear or not linear (e.g. exponential and polynomial)

DISCLOSURE OF THE INVENTION

These objects are achieved by the present invention, that relates to a chromatography apparatus, of the type comprising at least one capillary column and means to control the temperature of the column, characterized by comprising at least one element made of electrically conductive material to heat directly the capillary column, and by means for controlling the temperature of the capillary column comprising a control device operating according to a mathematical model having one component of predictive type, or of Feed Forward type, which describes the thermodynamic behavior of the assembly comprising the electrically conducting element and the column at least as a function of the thermal resistance and the thermal capacity of the cited assembly to regulate the supply of electrical energy to the conductive element.

The behavior of the conductive element is therefore simulated by one model component that takes account of the thermodynamic characteristics of the conductor/column assembly to determine what power must be applied to the conductive element to obtain the pre-established temperature at a given time. That in particular allows a fast response to unexpected variations of the temperature profiles set up for the analysis.

Beyond the predictive or Feed Forward type component, the model comprises also one component preferably of corrective or Feed Back type, to correct any errors of temperature that may be Introduced by the predictive component of the model.

Contrary to what happens in the known art, In which the control systems operate in feedback alone trying continuously to reach a series of equilibrium conditions, the system of the present invention operates according to a mathematical model that describes the thermodynamic behavior of the system under the form of a transfer function determined by two very well-defined algorithms.

The advantage of this approach is given by the greater contribution of power being determined a priori by the Feed Forward type model component, while a smaller contribution of power Is determined by the Feed Back type model component on the basis of the temperature error. In this way, the power determined by the Feed Back type model is considerably reduced and the control consequently turns out to be much more stable.

However, It must be taken into account that rapidity and precision are requirements that may be in conflict. In order to obtain rapidity of response it is necessary to supply instantaneously considerable power to the conductive element, while to obtain a certain precision it is opportune to supply limited amounts of power to the heating element over relatively longer times. Therefore, the powers determined on the basis of the two model components can also be "weighted" as a function of the requirement that needs to be privileged in any determined application According to a preferential aspect of the present invention, the temperature control device is able to cyclically update the parameters of the mathematical model and, in particular, at least the values of thermal capacity and thermal resistance.

This gives particularly high precision as far as the regulation of the temperature of the column directly heated by the conductive element is concerned.

In order to detect the temperature of the column, It is preferably used the same element In electrically conductive material destined for the heating of the column. The column and the conductive element are disposed In one covering sheath, In conditions of close mutuat contact for all the length contained Inside the same sheath. This allows effective thermal exchange to be maintained between conductive element and column for all their length and to limit thermal losses.

The covering sheath is preferably made of electrically Insulating material and the column/conductor/sheath assembly can be wrapped In coils without undesired short circuits occurring that might prejudice the correct operation of the system.

In a possible embodiment of the Invention, the element In electrically conductive material is made In the form of a filament. However, It must be understood that the system and the method for controlling the temperature according to the invention are applicable to any type of directly heated column assembly In which is present a conductive element made according to a different form.

Moreover, the control system adopted In the apparatus according to the present invention can also be used in the case in which a further conductive element Is used, separate from the heating element, to detect the temperature of the column.

The covering sheath is made from electrically insulating material and is preferably able to resist high temperatures, such as ceramic fibers or similar, for example.

Alternatively, the sheath can also be made from a thermo-shrinking type of material. The materials currently known having such characteristic, such as those known by the commercial name Teflon™ for example, can not support high temperatures much above 200° C., but this does allow the filament and the column to be easily introduced into the inside of the sheath before the assembly thus formed is subjected to heating to allow the contraction of the sheath and to obtain the desired close contact between column and filament.

The invention further relates to a method for controlling the temperature of a capillary column in a chromatography apparatus, characterized by providing for the use of at least one element made of electrically conductive material to heat directly the capillary column, and by the control of the temperature being carried out according to a mathematical model having a component of the predictive type, or Feed Forward type, which describes the thermodynamic behavior of the assembly comprising the electrically conductive element and the column at least as a function of the thermal resistance and the thermal capacity of said assembly to regulate the supply of electrical power to the conductive element.

BRIEF DESCRIPTION of DRAWINGS

Further features and advantages of the present invention will become clearer from the description that follows, which is made for illustrative and not limiting purpose with reference to the attached drawings, in which.

MODES FOR CARRYING OUT THE INVENTION

Figure 1:
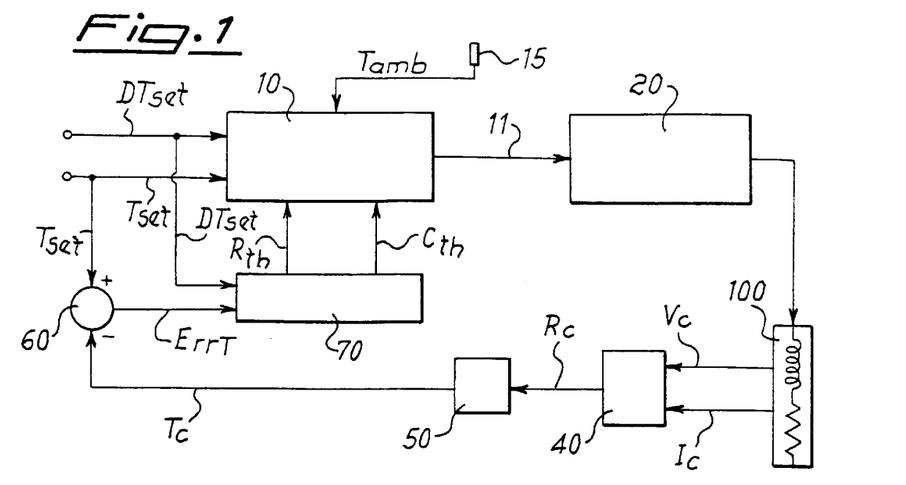
FIG. 1 is a block diagram of a system for temperature control in a chromatography apparatus according to the present invention.

The temperature control system illustrated in FIG. 1 comprises a functional block 10 able to memorize and update the relative parameters of the thermodynamic model of the assembly constituted by a conductive element 100, made for example in the form of a filament, and by a capillary column 200 (FIGS. from 3 to 5).

Figure 3:
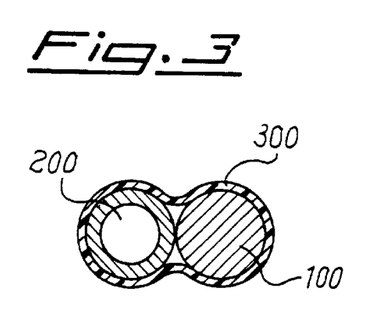
FIG. 3 is a cross-section view that shows one possible embodiment of the assembly comprising a capillary column and a conductive filament for heating the same.

According to the embodiment shown in FIG. 3, the conductive filament 100, made for example from metal such as nickel or other conductive material, is placed in close contact with the capillary column 200, made of fused silica for example, inside a sheath 300. In this case, filament 100 is also used as temperature sensor.

The covering sheath 300 is produced in electrically insulating material, such as, for example, ceramic fibers. Alternatively, materials can also be employed with characteristics compatible with particular requirements, such as a thermo-shrinking material (e.g. Teflon™), or polyamide or the like. The use of a thermo-shrinking type material could facilitate the fabrication of the assembly constituted by filament 100, column 200 and sheath 300, even if currently the greater part of the known thermo-shrinking materials are not particularly resistant to high temperatures.

The use of an electrically insulating material for the sheath allows the assembly comprising the filament, the column and the same sheath to be wrapped in coils without any contact occurring between various parts of the same filament, contact that would unavoidably prejudice the operation of the system.

The chosen configuration for filament 100 and column 200 inserted into sheath 300 allows the different expansions between filament 100 and column 200 to be compensated in function of the temperature even in the case in which the sheath/filament/column assembly is wrapped in coils.

Figure 4A:
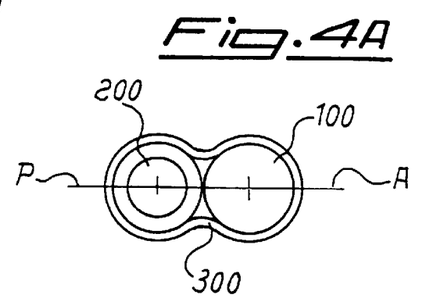
FIGS. 4A and 4B illustrate schematically the behavior of the column/filament assembly during operation of the apparatus according to the present invention.
Figure 4B:
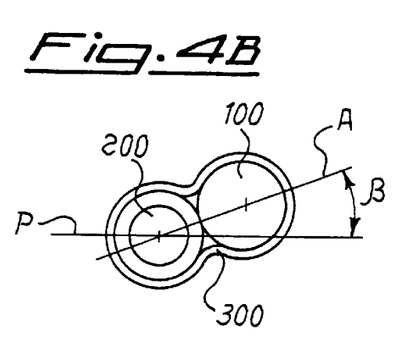

FIG. 4A shows the assembly at room temperature starting from a hypothetical condition of alignment of the straight line A that joins the centers of column 200 and filament 100 with respect to a horizontal plane P on which lies the straight line A corresponding to a given section, plane P on which also lies substantially one coil of the sheath/filament/column assembly in wrapped condition. Following the heating of the conductive filament 100, the greater thermal expansion of filament 100 transforms into a deformation of the assembly shown in FIG. 4B. In practice, filament 100 rotates with respect to column 200 causing the straight line A that connects the two centers to be inclined at an angle β with respect to plane P as a function of the difference of linear expansion to which filament and column in each coil are subject. The assembly is therefore equipped with an elastic geometry in which the different linear expansions of the conductive element 100 and column 200 are transformed into deformations that involve only slight variations of the mutual position of the conductive element and the column inside the sheath.

Returning again to FIG. 1, functional block 10 receives cyclically the information $DT_{set}$ and $T_{set}$ relative to the desired temperature profile, information coming from a data processing unit or data input device, for example, or from a dedicated controller already present in the chromatography apparatus (not shown).

In particular, $DT_{set}$ represents the desired temperature variation, i.e. the desired heating speed, while $T_{set}$ represents the instantaneous value of the set up temperature. Information on the ambient temperature $T_{amb}$ also reaches functional block 10 supplied by a suitable sensor 15. The separate supply of values $DT_{set}$ and $T_{set}$ allows advantageously even temperature profiles with non-linear features, for example profiles of temperature with exponential or polynomial features, to be set up and followed with particular precision.

The output 11 of the functional block 10 drives a power unit 20 able to supply to the heating element, such as filament 100 in conductive material, the voltage (and therefore the power) necessary to constantly follow the set up temperature profile with particular precision.

From the same filament 100, the voltage between terminals of the filament $V_C$ and current that circulates in it $I_C$ are measured every instant. These data are sent to a first calculation block 40 able to determine the instantaneous resistance $R_c$ of the filament that heats the column in relation to the data received by applying the well known Ohm's law, which gives in this case:

$$R_c = V_c/I_c \qquad (1)$$

The Rc value thus calculated is sent in its turn to a second calculation block 50 that determines the instantaneous temperature $T_c$ of column 200 placed in contact with filament 100. Ic can be calculated starting from the known relation that links the resistance of filament 100 to the temperature, i.e.:

$$R_c = R_{ref}*[1+\alpha*(T_c-T_{ref})] \qquad (2)$$

in which $R_c$ is the resistance of the filament at temperature $T_c$, $R_{ref}$ is the resistance of the same conductor at a reference temperature $T_{ref}$ and α is the coefficient of resistivity of the material from which the conductive filament is made as a function of the temperature. Resolving the equation (2) for $T_c$ gives:

$$T_c = [R_c - R_{ref}*(1-\alpha*T_{ref})]/\alpha*R_{ref} \qquad (3)$$

It is known that the value of the coefficient α can be considered constant only in a limited temperature range, but it is worth to take into account that this coefficient also varies as a function of the temperature. Therefore, $T_c$ according to equation (3) can for example be calculated on the basis of values of $T_c$ estimated and memorized in a table, using interpolation techniques for intermediate values. Alternatively, the values of coefficient α for each temperature can be memorized in a table or the variations Δα as a function of the temperature with respect to the value α considered constant.

The same calculation can be done for the value ρ of the specific resistivity of the material instead of the same resistance, taking into account the relation:

$$R = \rho*l/s \qquad (4)$$

In which is the length of the conductive filament and s is its section. The value $T_c$ thus determined from second calculation block 50 is cyclically compared in 60 with the value of the set-point temperature $T_{set}$ in such way as to determine the temperature error $Err_T$ between the set-point temperature and that effectively obtained at a given step.

The value corresponding to the temperature error $Err_T$ is taken as input to a block 70 that has the function of "observer", together to $DT_{set}$ value of the derivative of the temperature profile to be followed.

According to these data received as input, i.e. in function of the temperature error and of the trend of the same temperature in the time, the observer block 70 determines the new values of thermal resistance $R_{th}$ and thermal capacity $C_{th}$ that must be sent as input to functional block 10 in order to update the parameters of the mathematical model that describes the thermodynamic behavior of filament 100 and to permit correct control of the power unit 20.

All the cyclical operations are repeated at high frequency, for example with a period less than a millisecond, so as to obtain high precision of reproduction of the desired temperature profile.

Beyond guaranteeing high precision, the control system according to the present invention allows—even at operational speed—temperature profiles with particularly high heating speeds to be followed easily (for example heating speed up to approximately 25° C./s) while maintaining a good precision.

In order to obtain the initial parameters of the mathematical model it is possible for example to determine the resistance of filament 100 at a first pre-established temperature and therefore to establish the variation of the resistance of the filament when the same is taken to a second pre-established temperature, different from the previous one, according to a pre-established way, for example by applying a step variation to the power supplied to the heating element. This allows the initial values of thermal resistance and thermal capacity of the model to be found, as well as the length of the column to be calculated if the cross-section of filament 100 is known or, if this is not known, for example, the effective length of column 200 to be determined, or to verify that the length of column 200 associated with heating filament 100 is effectively that pre-established.

Figure 6:
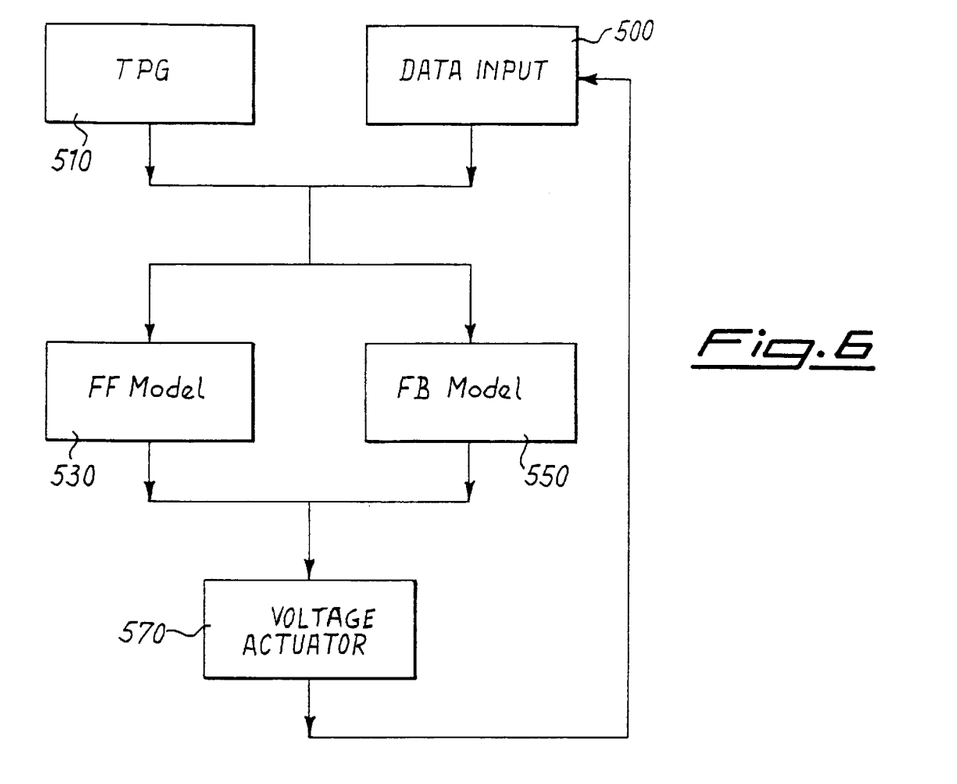
FIG. 6 is a functional diagram showing the logic of the model of a control system for an apparatus according to the present invention.

FIG. 6 shows a functional diagram of a model that can be applied to every iteration of the system. The blocks shown in this diagram, taken as a whole, control the power supplied to the system, in the form of a supply voltage $V_{sup}$, and therefore control the temperature of the column.

The model comprises for example a DATA INPUT block, indicated by reference 500, that acquires a number of input variables at step n−1 and a TPG (Temperatures Profiles Generator) block, indicated by reference 510, which generates the desired temperature profiles, i.e. not only linear profiles of temperature (isotherms and ramps) but also exponential or polynomial profiles.

The data coming from blocks 500 and 510 are supplied to blocks 530 (FF Model) and 550 (FB Model) which represent respectively the predictive component of Feed Forward type and the corrective component of Feed Back type of the model. The latter calculate what power will have to be supplied to the heating element of the column at step n by block 570 (Voltage Actuator) which is the actuator of the supply voltage $V_{sup}$. In other words, $V_{sup}^{(n)}$ represents the supply voltage that must be supplied to the system in its entirety, not only to supply power to the column and thus obtain the $T_{set}^{(n)}$, temperature, i.e. the desired set-point temperature at step n, but also to supply the control circuit.

Figure 7:
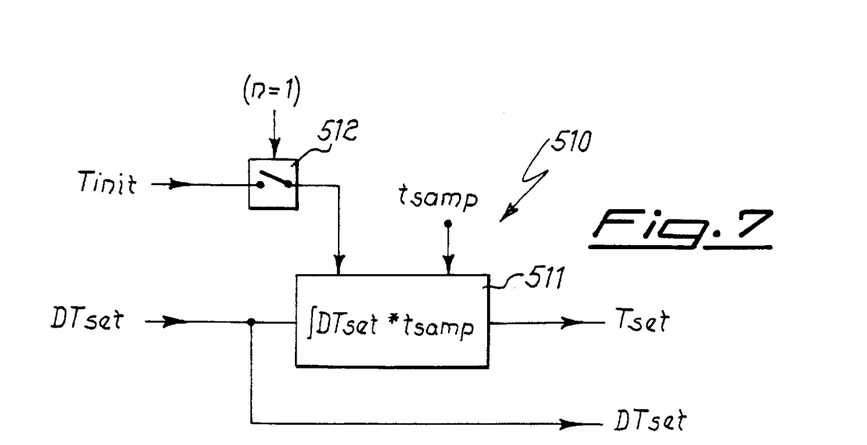
FIG. 7 is a diagram of the temperature profile generator block of the model in FIG. 6.

In FIG. 7 the scheme of block 510 that generates the desired temperature profiles is shown in more detail. In particular, block 510 generates the correct sequence of set points that describe a desired temperature profile.

In practice, the temperature profile generator is an integration algorithm that can be described by the equation:

$$T_{set}^{(n)} = T_{set}^{(n-1)} + DT_{set} \cdot t_{samp} \tag{5}$$

in which $T_{set}^{(n)}$ is the desired temperature at step n, $T_{set}^{(n-1)}$ is the temperature detected at the previous step n−1, $DT_{set}$ is the rate of change of the temperature and $t_{samp}$ is the sampling period.

Therefore, values $DT_{set}$ and $t_{samp}$, as well as initial temperature value $T_{init}$ that is only considered at the initial moment (step n=1) of the control, reach the integrator block 511 of FIG. 7. Logical operator 512 therefore represents a condition that occurs only at the initial moment, when it is necessary to know the starting temperature.

Figure 8:
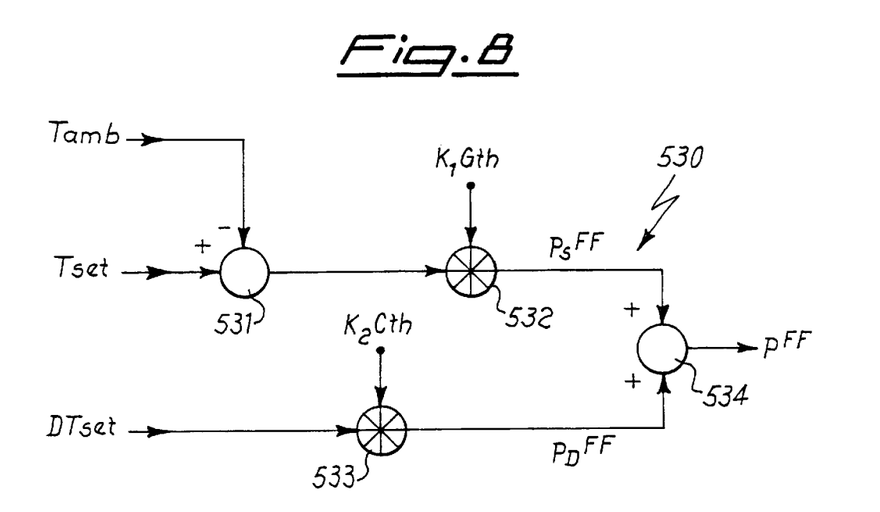
FIG. 8 is a diagram of the Feed Forward block of the model in FIG. 6.

FIG. 8 shows the predictive component 530 of the model or FF model. This model component is used to predict the power which needs to be supplied to the system to obtain a given temperature $T_{set}$ when the system is subject to a heating speed of $DT_{set}$. In practice, the two components—static power $P_S$ (in constant temperature condition) and dynamic power $P_D$ (in variable temperature condition whether linear or non-linear)—to be supplied at step n are calculated taking account of the thermal resistance $R_{th}$ and the thermal capacity $C_{th}$ of the system, as well as the ambient temperature $T_{amb}$ in which the system operates.

Static power $P_S^{FF}$ calculated according to the model Feed Forward is given by the equation:

$$P_S^{FF} = (T_{set} - T_{amb}) \cdot G_{th} \tag{6}$$

in which $G_{th}$ is linked to the thermal resistance $R_{th}$ by the relation:

$$G_{th} = (R_{th})^{-1} \tag{7}$$

In the model of FIG. 8, a subtraction operator 531 calculates the difference between the set temperature $T_{set}$ and the ambient temperature $T_{amb}$, while a multiplication operator 532 multiplies the difference thus calculated by factor $G_{th}$ to give static power $P_S^{FF}$.

Dynamics power $P_D^{FF}$ calculated according to the Feed Forward model instead is given by the equation:

$$P_D^{FF} = DT_{set} \cdot C_{th} \tag{8}$$

The values of $C_{th}$ and $R_{th}$ are recalculated at every iteration of the model to follow the change of physical characteristics of the system which vary with the varying temperature.

The model of FIG. 8 therefore provides for a multiplication operator 533 that multiplies factor $DT_{set}$ and factor $C_{th}$ to give dynamic power $P_D^{FF}$ calculated according to the Feed Forward model.

The total power $P^{FF}$ calculated according to the Feed Forward model is given therefore by the sum of static power $P_S^{FF}$ and of dynamic power $P_D^{FF}$, i.e.:

$$P^{FF} = P_S^{FF} + P_D^{FF} \tag{9}$$

A sum operator 534 is therefore provided that calculates power $p^{FF}$ as output.

Figure 9:
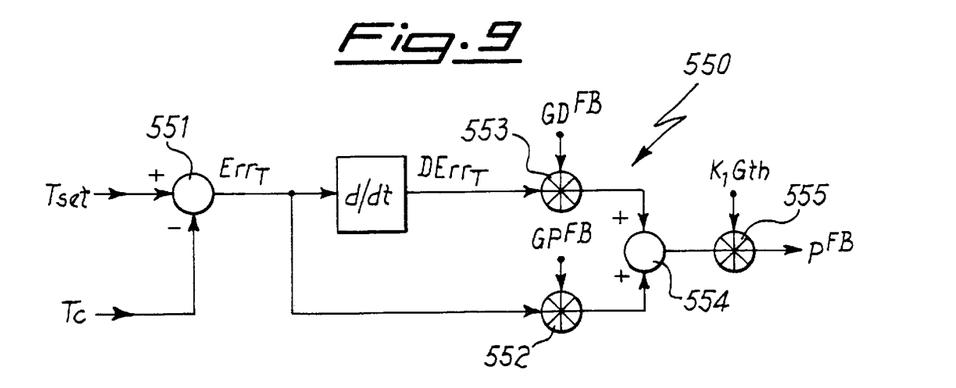
FIG. 9 is a diagram of the Feed Back block of the model in FIG. 6.

FIG. 9 shows the corrective component 550 of the model or FB model. In practice the Feed Back component of the model supplies a corrective effect on the power calculated in Feed Forward taking account of the static temperature error $Err_T$ and of its first derivative $DErr_T$ with respect to time.

In practice, factor $Err_T$ is given by the difference between the set-point temperature $T_{set}^{(n-1)}$ set at the previous step and the column temperature $T_c^{(n-1)}$ effectively detected at the same previous step, i.e.:

$$Err_T = T_{set}^{(n-1)} - T_c^{(n-1)} \tag{10}$$

The subtraction operator 551 shown in FIG. 9 calculates this difference.

In the correction of the power set at the step n, based on temperature errors found at the previous step (n−1) account must however be taken of the feedback system gain or, more properly, account must be taken separately of proportional gain $GP^{FB}$ and derivative gain $GD^{FB}$ of the Feed Back model.

The proportional contribution of the temperature error of $\Delta T_P$, calculated taking account of the proportional gain, is given by the following relation:

$$\Delta T_P = \text{Err}_T * GP^{FB} \tag{11}$$

The two factors of the product, of which $GP^{FB}$ represents a dimensionless coefficient, are applied to the multiplication operator 552 in FIG. 9.

The derivative contribution of the error of temperature $\Delta T_D$, calculated taking account of the derivative gain, is given by the relation:

$$\Delta T_D = (d\text{Err}_T/dt) * GD^{FB} \tag{12}$$

The two factors of the product (in this case $GD^{FB}$ has dimensions °C./sec), are applied to the multiplication operator 553.

The sum of contributions $\Delta T_P$ and $\Delta T_D$, obtained by means of the sum operator 554, is therefore multiplied by factor $G_{th}$ through the multiplication operator 555, to give as output the corrective power $P^{FB}$ determined on the basis of the components of Feed Back model from the relation:

$$P^{FB} = (\Delta T_P + \Delta T_D) * G_{th} \tag{13}$$

Figure 10:
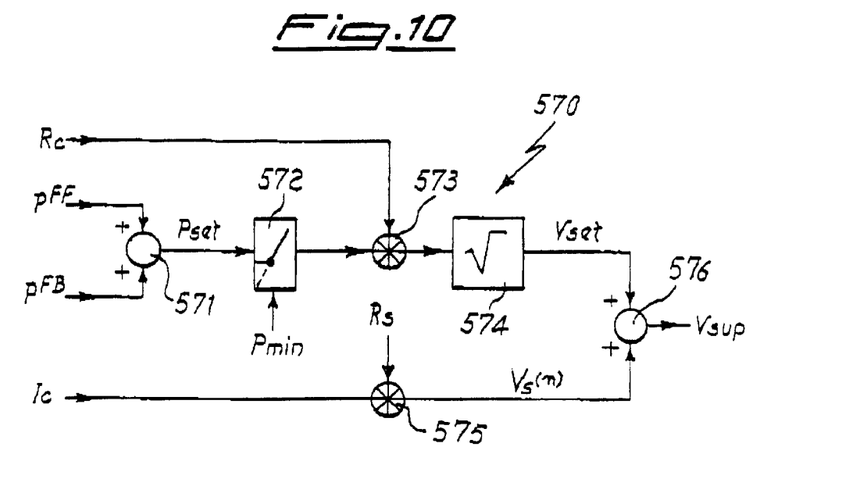
FIG. 10 is a diagram of the voltage actuator block of the model in FIG. 6.

FIG. 10 shows voltage actuator 570 of the supply voltage $V_{sup}$ that allows to calculate the supply voltage to be applied to the entire system as a function of the power calculated on the basis of the predictive model ($P^{FF}$) and the corrective model ($P^{FB}$), SO that the column reaches the desired set-point temperature of $T_{set}^{(n)}$ at step n.

It should be emphasized that in the calculation of $V_{sup}$ it is also necessary to take account of the internal resistance $R_S$ of the control system. The value of $R_S$ depends on the same control circuit and can also be affected for example by the construction of the power/measurement terminals applied to the heating element of the column.

The total power $P_{set}$ to be applied to the system at step n is given by the sum of the power calculated on the basis of the predictive and corrective models, i.e.:

$$P_{set} = (P^{FF}) + (P^{FB}) \tag{14}$$

Even if not expressly shown in FIG. 10, such powers can also be "weighted" before being added, in such a way as to privilege one or more characteristics with respect to others, for example the speed of response with respect to the precision, or vice versa.

In the scheme of FIG. 10, a logical operator 572 could be provided (even though it is not absolutely necessary) in series with the sum operator 571 predisposed to sum the factors (weighed or not) in relation (14). This latter makes it possible (if necessary) to maintain nonetheless a minimal power $P_{min}$ whenever the calculated power $P_{set}$ is less than the same minimal power.

The calculation of the voltage $V_{set}$ to be applied to the heating element of the column at step n is preferably given by means of the relation:

$$V_{set} = (P_{set} * R_c)^{1/2} \tag{15}$$

in which $R_c$ is the resistance of the column, or rather of its heating element, measured at the previous step (n−1). The multiplication operator 573 and the square root extraction operator 574 implement this relation.

The calculation according to relation (15) achieves better precision than other possible formulas because the resistance Rc varies very little between successive sampling steps, even in case of sudden variations of the desired heating speed. In fact, if for example, $V_{set}$ were estimated as ratio between Pset (supply power at step n) and $l_c$ (column current measured at step n−1) could give rise to problems above all at the transient steps of $P_{set}$ because of the high variability of $l_c$ between successive samplings.

As already mentioned previously, in order to obtain the total supply voltage $V_{sup}$ at step n it is necessary to take account of the internal resistance $R_s$ of the system, i.e. the resistance measured at the connection terminals of the heating element should ideally be removed from the total circuit. The resistance $R_s$ is generally much smaller than $R_c$ and its variations therefore are still more limited than $R_c$ between successive samplings It is legitimate therefore to calculate the resistance $R_s$ of the system at step n on the basis of the values $V_{sup}^{(n-1)}$, $V_c^{(n-1)}$ and $l_c^{(n-1)}$ measured at step (n−1) using the relation:

$$R_s^{(n)} = (V_{sup}^{(n-1)} - V_c^{(n-1)})/l_c^{(n-1)} \tag{16}$$

Consequently, the voltage $V_s^{(n)}$ of the system at step n can therefore be calculated with limited error on the basis of the relation:

$$V_s^{(n)} = R_s^{(n)} * l_c^{(n-1)} \tag{17}$$

The multiplication operator 575 supplies as output the value $V_s^{(n)}$—the product of the two factors indicated above—which becomes input for the sum operator 576 that finally supplies as output the value $V_{sup}^{(n)}$ adding it to the value $V_{set}^{(n)}$ calculated for the column, i.e.:

$$V_{sup}^{(n)} = V_{set}^{(n)} + V_s^{(n)} \tag{18}$$

The total voltage $V_{sup}^{(n)}$ that the system must supply at step n to give the necessary power to the same control circuit and the column is thus calculated.

The cyclical updating of the values of thermal resistance $R_{th}$ and thermal capacity $C_{th}$ of the column can be accomplished at every step in various ways.

For example, it has already been shown that the power $P_{set}$ supplied to the column heating element in a certain step can be considered as the sum of the static power Ps and the dynamic power $P_D$. In practice, the power $P_{set}^{(n-1)}$ that has been supplied at step (n−1) will be given by the relation::

$$P_{set}^{(n-1)} = P_S^{(n-1)} + P_D^{(n-1)} \tag{19}$$

Considering that the effects of the power supplied at step (n−1) are detected at the next step n, the relation that expresses the static power as a function of the new $R_{th}^{(n)}$ parameter is the following:

$$P_S^{(n-1)} = (T_{set}^{(n)} - T_{amb}^{(n)})/R_{th}^{(n)} \tag{20}$$

in which $T_{set}^{(n)}$ and $T_{amb}^{(n)}$ represent respectively the desired column temperature at step n and the ambient temperature at step n.

On the basis of the same consideration, the supplied dynamic power at the step (n−1) is the following:

$$P_D^{(n-1)} = (T_{set}^{(n)} - T_{set}^{(n-1)})/t_{samp} * C_{th}^{(n)} \tag{21}$$

in which $T_{set}^{(n)}$ and $T_{set}^{(n-1)}$ are the temperatures desired respectively at steps n and (n−1), and $t_{samp}$ represents the sampling period.

Figure 11:
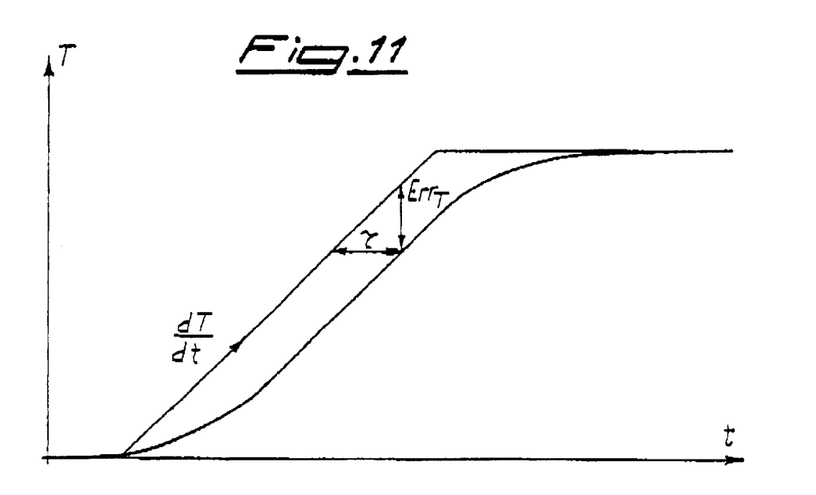
FIG. 11 is a diagram that schematically illustrates the change of temperature over time compared with a simple temperature profile.

Moreover, it is known that exists the following relation between $R_{th}$ and $C_{th}$:

$$\tau = R_{th} * C_{th} \quad (22)$$

in which τ represents the mean delay within which the column reaches a desired temperature $T_{set}$, for example during a ramp. In practice, as it is also obvious from FIG. 11, the value τ can easily be calculated at any time taking account of the relation:

$$\tau*(dT/dt) = \mathrm{Err}_T \quad (23)$$

in which the factor dT/dt is the slope of the desired profile (the rate of change of temperature) and $\mathrm{Err}_T$ is the temperature error at a certain step, i.e. the difference between the set temperature $T_{set}$ and the effective temperature $T_c$ of the column.

Resolving equations (19)-(23) for $R_{th}$ and $C_{th}$, the new values of thermal resistance and thermal capacity are found that must be used in the model at step n, eventually providing also an opportune weighted adaptation for these variable parameters. This represents, however, only one possibility of determination of the values of $R_{th}$ and $C_{th}$ and is supplied purely by way of example.

Figure 12:
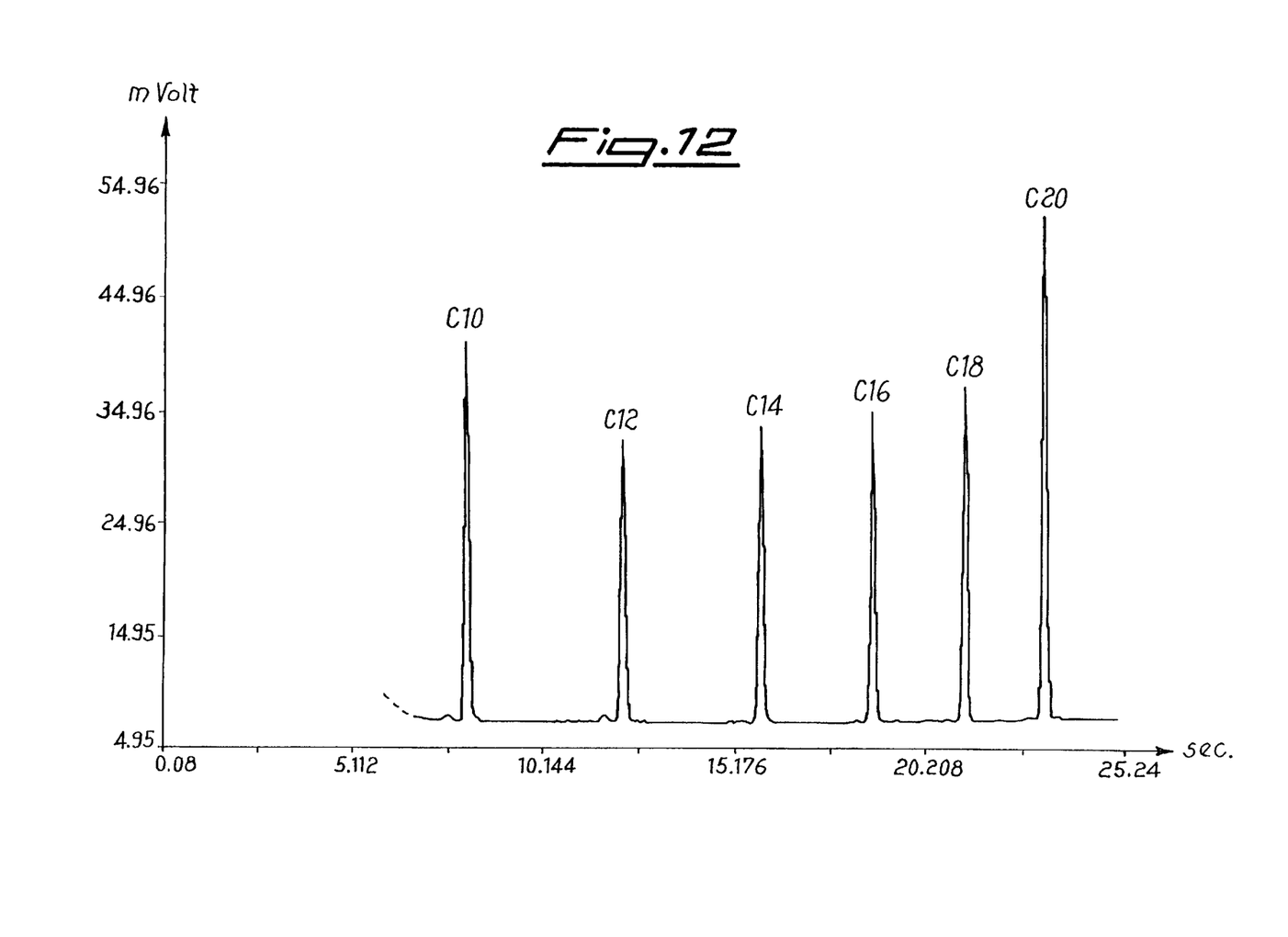
FIG. 12 shows a chromatogram of a test analysis carried out with a system according to the present invention.

FIG. 12 shows a chromatogram of a test analysis carried out on a mixture containing $C_{10}$–$C_{20}$ in $C_6$, employing $H_2$ as carrier.

The test was carried out using a capillary column 1.2 m in length, with internal diameter of 0.25 μm and external diameter of 0.1 mm. The gas chromatography apparatus was equipped with a split type injector with pressure of 114 kPa, flow of 1 cc/min at a temperature of 250° C.; the output detector was of FID type maintained at a temperature of 300° C.

The temperature profile was set up for 0.1 min to 80° C. and was increased until a temperature of 250° C. with a variation speed of 10° C./sec.

As can be seen in FIG. 12, in which the initial solvent part of the elution is not shown, the peaks of compounds $C_{10}$–$C_{20}$ are very narrow, of the approximate order of 1/10 second. Taking this fact into consideration, and also the fact that the analysis only lasts approximately 24 seconds, the peaks are very well defined, thus proving the validity of the temperature control system according to the present invention.

Furthermore, repeatability tests were done under the same conditions reported above, for both the areas of the peaks and the retention times.

Table 1 shows the result of the tests done on 20 analyses of samples with the same $C_{10}$–$C_{20}$ composition to estimate the repeatability of the peak areas.

TABLE 1

| Compound | Mean Peak Area (μVolt * sec) | Relative Standard Deviation (%) |
| --- | --- | --- |
| $C_{10}$ | 41840.5 | 1.44 |
| $C_{12}$ | 33701.8 | 1.71 |
| $C_{14}$ | 36509.6 | 1.53 |
| $C_{16}$ | 36838.4 | 1.59 |
| $C_{18}$ | 37024.6 | 1.99 |
| $C_{20}$ | 54709.7 | 2.1 |

Table 2 shows the result of the tests done on 20 analyses of samples with the same $C_{10}$–$C_{20}$ composition to estimate the repeatability of the retention times of the peaks.

TABLE 2

| Compound | Retention times (sec.) | Relative Standard Deviation (%) |
| --- | --- | --- |
| $C_{10}$ | 8.21 | 0.43 |
| $C_{12}$ | 12.31 | 0.32 |
| $C_{14}$ | 15.94 | 0.21 |
| $C_{16}$ | 18.88 | 0.17 |
| $C_{18}$ | 21.29 | 0.17 |
| $C_{20}$ | 23.34 | 0.13 |

As can be seen, results of both of the tests done show good repeatability of both parameters investigated.

Figure 2:
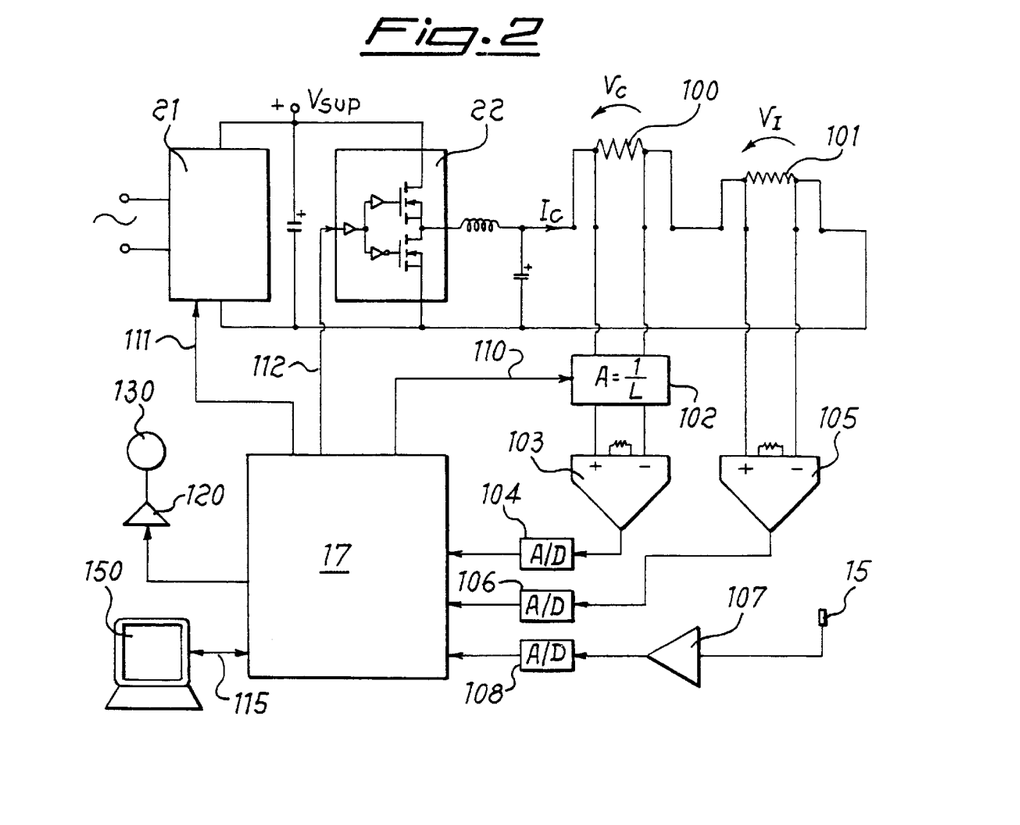
FIG. 2 is a circuit diagram of the system shown in FIG. 1.

FIG. 2 shows a circuit diagram of a temperature control system according to the present invention. The system comprises in particular a main power section 21 that receives electrical power from a source, for example the mains, and is able to distribute the voltage $V_{sup}$ necessary to the operation of the system, among which in particular the voltage necessary to supply section 22 which supplies electrical power to heating element 100 of column 200.

The analogue value of voltage $V_C$ applied to heating element 100 is determined at the terminals of the same, while the analogue value of current $1_c$ that circulates in heating element 100 is determined by a measurement resistor 101 (or shunt) in the form of the voltage $V_I$ at its terminals. The value of $V_C$ measured at the terminals of heating element 100 is preferably standardized with respect to the length of the same element corresponding to section 102. This standardized value is amplified in 103 before being converted to digital form by an A/D converter 104 and being sent as input to a micro-controller or a DSP (Digital Signal Processor) indicated with reference 17. As already pointed out, the information on the length of heating filament 100 can easily be calculated in the starting phase of the system and memorized in micro-controller or DSP 17, which then sends it to block 102 through link 110.

The analogue value of $1_c$, shown in the form of the voltage $V_I$ across resistor 101, is amplified in 105 before being converted to digital form by an A/D converter 106 and being sent as input to micro-controller or DSP 17.

Micro-controller or DSP 17 moreover also receives the value of the ambient temperature from sensor 15 under the form of a converted analogue signal that is first amplified in 107 and then converted into digital form by an A/D converter 108.

Micro-controller or DSP 17 comprises two output lines 111 and 112 that go respectively to control the main supply section 21, that commands the variation of the supply voltage $V_{sup}$ to the system, and supply section 22 which is designed to supply the correct voltage to heating element 100. Micro-controller or DSP 17 can moreover communicate through the bi-directional line 115 with an external unit 150 for processing or inputting data.

Figure 5:
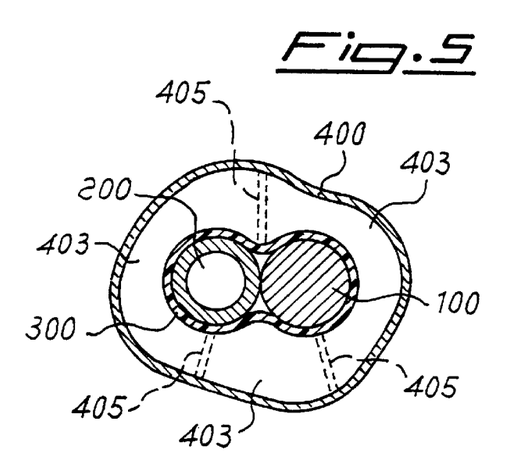
FIG. 5 is a cross-section view that illustrates another possible embodiment of the assembly comprising a capillary column and a conductive filament for the heating of the same.

A possible embodiment of the present invention provides for micro-controller or DSP 17 moreover to control the electric motor of an impeller 130 through a suitable driver circuit 120. Alternatively, an electro-valve can be set in action that controls the flow of a cooling gas. As shown in FIG. 5, the assembly constituted by filament 100, column 200 and the covering sheath 300 is preferably lodged in a slack way inside a tubular container 400 to allow the air moved by impeller 130, or the cooling gas supplied through an appropriate electro-valve, to circulate in the space 403 comprised between the inner wall of the tubular covering 400 and the external wall of the covering sheath 300. Spacers 405 (shown by broken line in FIG. 5) can be associated to container 400 with substantially radial alignment to avoid interruptions of the airflow driven by impeller 130. According to this aspect of the present invention, it is possible to accelerate the cooling of column 200.

What is claimed is:

1. A method for controlling temperature of a capillary column in a chromatography apparatus, comprising directly heating said capillary column with at least one electrically conductive element made of electrically conductive material, and carrying out control of the temperature according to a mathematical model having a component of predictive or Feed Forward which describes thermodynamic behavior of an assembly comprising said electrically conductive element and said column at least as a function of thermal resistance and thermal capacity of said assembly to regulate supply of electrical power to said at least one electrically conductive element.

2. A method according to claim 1, wherein said mathematical model comprises a further component of corrective or Feed Back.

3. A method according to claim 1, wherein parameters of said mathematical model are cyclically updated.

4. A method according to claim 3, wherein the parameters of said model are cyclically calculated and updated on the basis of information relating to the temperature profile that is desired to be obtained in time, said information comprising at least an instantaneous value of the temperature and at least an instantaneous value of its derivative with respect to time.

5. A method according to claim 1, wherein said capillary column and said at least one electrically conductive element are disposed inside a covering sheath in close mutual contact.

6. A method according to claim 5, wherein said at least one electrically conductive element is made in a form of a filament.

7. A method according to claim 6, wherein the assembly is constituted by said capillary column, said filament and said covering sheath lodged inside a tubular container.

8. A method according to claim 7, wherein circulation of a thermal exchange fluid in space comprised between an inner wall of said tubular container and an external wall of said covering sheath is provided for.

9. A method according to claim 5, wherein said covering sheath is made of electrically insulating material.

10. A method according to claim 9, wherein said covering sheath is made of ceramic fibers.

11. A method according to claim 9, wherein said covering sheath is made of a thermo-shrinking material.

12. A method according to claim 5, characterized by cyclically determining temperature inside said covering sheath as a function of voltage applied to terminals of said at least one electrically conductive element and of current that circulates in said at least one electrically conductive element.

13. A method according to claim 1, further providing for the measurement of the temperature of said capillary column.

14. A method according to claim 5, wherein the temperature of said capillary column is detected by means of said at least one electrically conductive element.

15. A method according to claim 1, characterized by cyclically detecting the voltage applied to terminals of said electrically conductive element and the current that circulates in said conductive element.

16. A method according to claim 1, characterized by cyclically determining the resistance of said at least one electrically conductive element as a function of the voltage applied to terminal of said at least one electrically conductive element and of the current that circulates in said at least one electrically conductive element.

17. A chromatography apparatus comprising at least one capillary column, at least one electrically conductive element made of electrically conductive material to heat directly said at least one capillary column, means for controlling temperature of said capillary column comprising a control device that operates according to a mathematical model having one component of predictive or Feed Forward which describes thermodynamic behavior of an assembly comprising said at least one electrically conductive element and said column at least as a function of thermal resistance and thermal capacity of said assembly in order to regulate supply of electrical power supplied to the at least one electrically conductive element.

18. An apparatus according to claim 17, wherein said mathematical model further comprises a component of corrective or Feed Back.

19. An apparatus according to claim 17, wherein said control device is configured to cyclically update parameters of said mathematical model.

20. An apparatus according to claim 17, wherein said means for controlling the temperature of said capillary column comprise at least one device configured to cyclically determine voltage applied to terminals of said at least one electrically conductive element and current that circulates in said at least one electrically conductive element.

21. An apparatus according to claim 17, wherein said means for controlling the temperature of said capillary column comprise at least one device configured to determine cyclically electrical resistance of said at least one electrically conductive element as a function of voltage applied to terminals of said at least one electrically conductive element and current that circulates in said at least one electrically conductive element.

22. An apparatus according to claim 17, wherein said means for controlling the temperature of said capillary column comprise at least one device configured to determine cyclically the temperature of said capillary column as a function of voltage applied to terminals of said at least one electrically conductive element and current that circulates in said at least one conductive element.

23. An apparatus according to claim 17, further comprising means for detecting the temperature of said capillary column.

24. An apparatus according to claim 23, wherein said means for detecting the temperature of said capillary column comprise said at least one electrically conductive element and wherein said at least one capillary column and said at least one electrically conductive element are disposed in a covering sheath in close mutual contact for all the length contained inside said sheath.

25. An apparatus according to claim 24, wherein said at least one electrically conductive element is produced in a form of a filament.

26. An apparatus according to claim 24, comprising a tubular container inside of which is lodged the assembly, the assembly being constituted by said capillary column, said filament and said covering sheath.

27. An apparatus according to claim 26, wherein means are provided for conveying and circulating a thermal exchange fluid in the space comprised between the inner wall of said tubular container and the external wall of said covering sheath.

28. An apparatus according to claim 24, wherein said covering sheath is made of an electrically insulating material.

29. An apparatus according to claim 24, wherein said covering sheath is made of ceramic fibers.

30. An apparatus according to claim 24, wherein said covering sheath is made of a thermo-shrinking material.

* * * * *